(12) United States Patent
Poplaw

(10) Patent No.: US 11,684,348 B1
(45) Date of Patent: Jun. 27, 2023

(54) SYSTEM FOR COLOR-CODING MEDICAL INSTRUMENTATION AND METHODS OF USE

(71) Applicant: Clear Biopsy LLC, St. Joseph, MO (US)

(72) Inventor: Steven Poplaw, St. Joseph, MO (US)

(73) Assignee: Clear Biopsy LLC, St. Joseph, MO (US)

( * ) Notice: Subject to any disclaimer, the term of this patent is extended or adjusted under 35 U.S.C. 154(b) by 0 days.

(21) Appl. No.: 18/047,871

(22) Filed: Oct. 19, 2022

Related U.S. Application Data

(63) Continuation of application No. PCT/US2022/012716, filed on Jan. 18, 2022.

(60) Provisional application No. 63/285,240, filed on Dec. 2, 2021.

(51) Int. Cl.
| | |
|---|---|
| *A61B 10/02* | (2006.01) |
| *A61B 17/34* | (2006.01) |
| *A61B 8/00* | (2006.01) |
| *G06T 7/10* | (2017.01) |
| *G06N 3/02* | (2006.01) |
| *G06N 20/00* | (2019.01) |

(52) U.S. Cl.
CPC .......... *A61B 10/0233* (2013.01); *A61B 8/468* (2013.01); *A61B 17/3403* (2013.01); *G06T 7/10* (2017.01); *A61B 2017/3413* (2013.01); *G06N 3/02* (2013.01); *G06N 20/00* (2019.01); *G06T 2207/10132* (2013.01); *G06T 2207/20081* (2013.01)

(58) Field of Classification Search
CPC . A61B 10/0233; A61B 8/468; A61B 17/3403; A61B 2017/3413; G06T 7/10; G06T 2207/10132; G06T 2207/20081
See application file for complete search history.

(56) References Cited

U.S. PATENT DOCUMENTS

| | | | |
|---|---|---|---|
| 9,642,592 B2 | 5/2017 | Wang et al. | |
| 10,434,278 B2 | 10/2019 | Dunbar et al. | |
| 10,758,205 B2 | 9/2020 | Greppi et al. | |
| 2004/0002653 A1* | 1/2004 | Greppi | A61B 8/483 600/431 |
| 2011/0190660 A1* | 8/2011 | Levy | A61B 10/0275 600/566 |
| 2018/0158209 A1* | 6/2018 | Fine | G06T 7/75 |
| 2019/0088359 A1* | 3/2019 | Moore | G06F 16/5838 |
| 2019/0378293 A1* | 12/2019 | Mwikirize | G06T 5/20 |
| 2021/0000553 A1* | 1/2021 | St. Pierre | G06N 20/00 |

(Continued)

*Primary Examiner* — Rene T Towa
(74) *Attorney, Agent, or Firm* — Bookoff McAndrews, PLLC

(57) ABSTRACT

A system comprising a biopsy needle device comprising a cannula comprising a distal end configured to sever a tissue sample, and a trocar disposed within the cannula comprising a notch configured to retain a tissue sample, wherein at least one of the cannula and the trocar is divided into at least two segments including different echogenic coatings, an ultrasound probe, and a processor configured and arranged to collect images from the ultrasound probe and color code the at least two segments based on at least one characteristic relating to different echogenic coatings, surface textures, surface contours and dimensions of the biopsy device.

20 Claims, 10 Drawing Sheets
(4 of 10 Drawing Sheet(s) Filed in Color)

(56) References Cited

U.S. PATENT DOCUMENTS

2021/0401407 A1\* 12/2021 Yang .................... A61B 8/5207
2022/0101034 A1\* 3/2022 Ekin ......................... G06T 7/11

\* cited by examiner

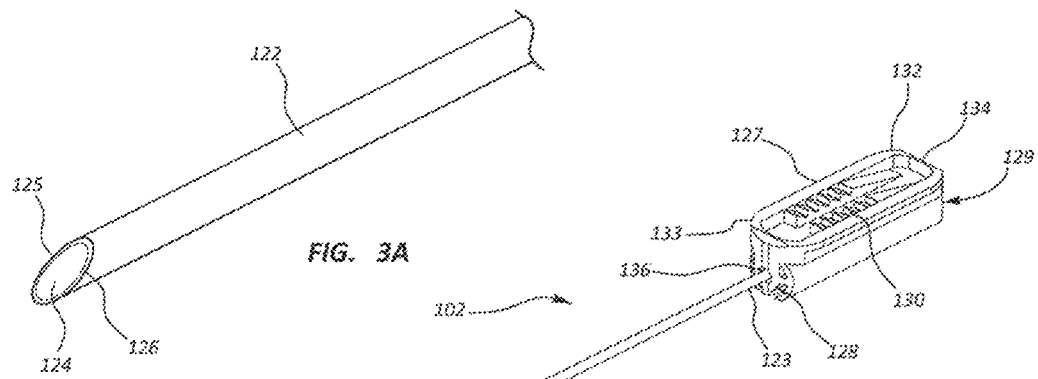
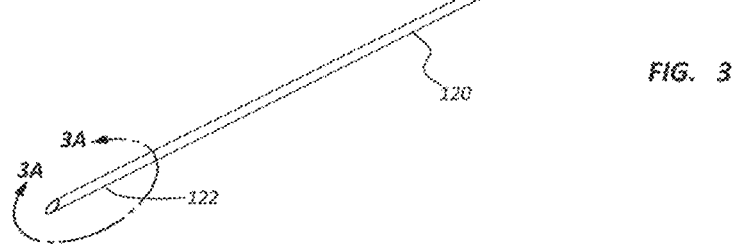
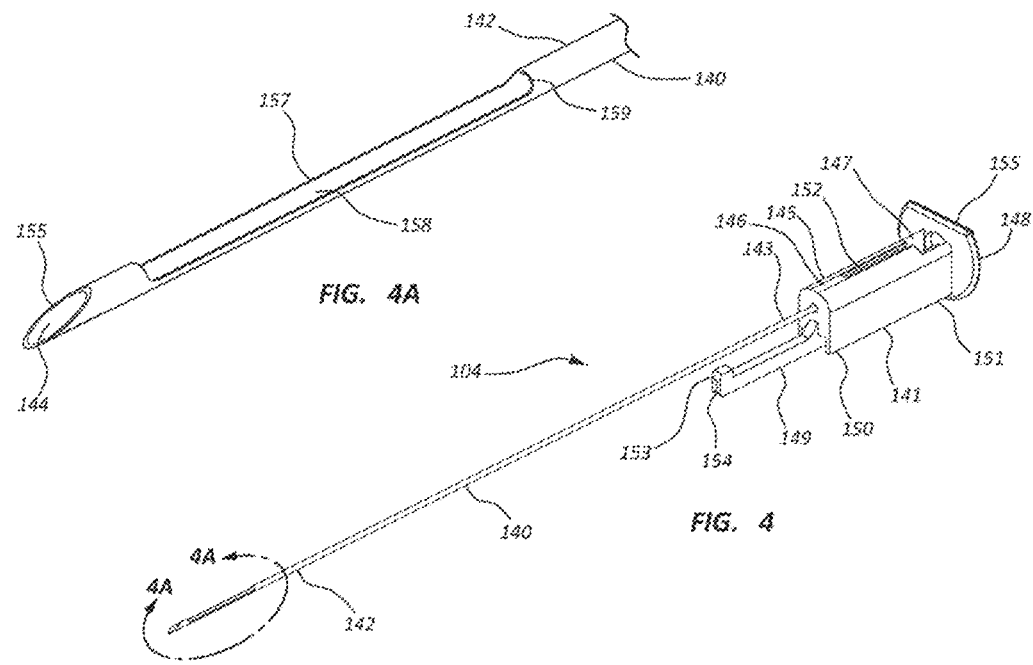

SYSTEM FOR COLOR-CODING MEDICAL INSTRUMENTATION AND METHODS OF USE

CROSS-REFERENCE TO RELATED APPLICATIONS

This application claims the benefit of priority under 35 U.S.C. 111(a) to PCT Application No. PCT/US2022/12716, filed on Jan. 18, 2022, which claims the benefit of priority to U.S. Patent Application No. 63/285,240, filed on Dec. 2, 2021, all of which are incorporated herein by reference in their entireties.

TECHNICAL FIELD

The present disclosure relates generally to medical devices. More specifically, the present disclosure relates to color-coded instrumentation, such as biopsy needle assemblies configured for use with tissue biopsy devices.

BACKGROUND OF THE DISCLOSURE

Medical procedures are often performed inside the body where the target and/or the instrument are hidden from the naked eye. Ultrasound is often used to provide imaging inside the body before, during or after such procedures, but such imaging is often grayscale. It is difficult for laypersons and young trainees to properly appreciate details from these grayscale images. In fact, depending on the circumstances, even seasoned professionals may improperly glean certain shadows or tones in the grayscale images. This may present patient safety issues and lead to injury or death. It may also prolong the length of a procedure as the physician or operator struggles to properly position instruments. The quality of the imaging may also lead to missing suspicious lesions or yielding false negative biopsies.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

FIG. 3 is a perspective view of a cannula of the biopsy needle device of FIGS. 1 and 2;

FIG. 3A is a detail view of a distal end portion of the cannula of FIG. 3 taken through line 3A;

FIG. 4 is a perspective view of a trocar of the biopsy needle device of FIGS. 1 and 2;

FIG. 4A is a detail view of the distal end of the trocar;

DETAILED DESCRIPTION

Figure 1:
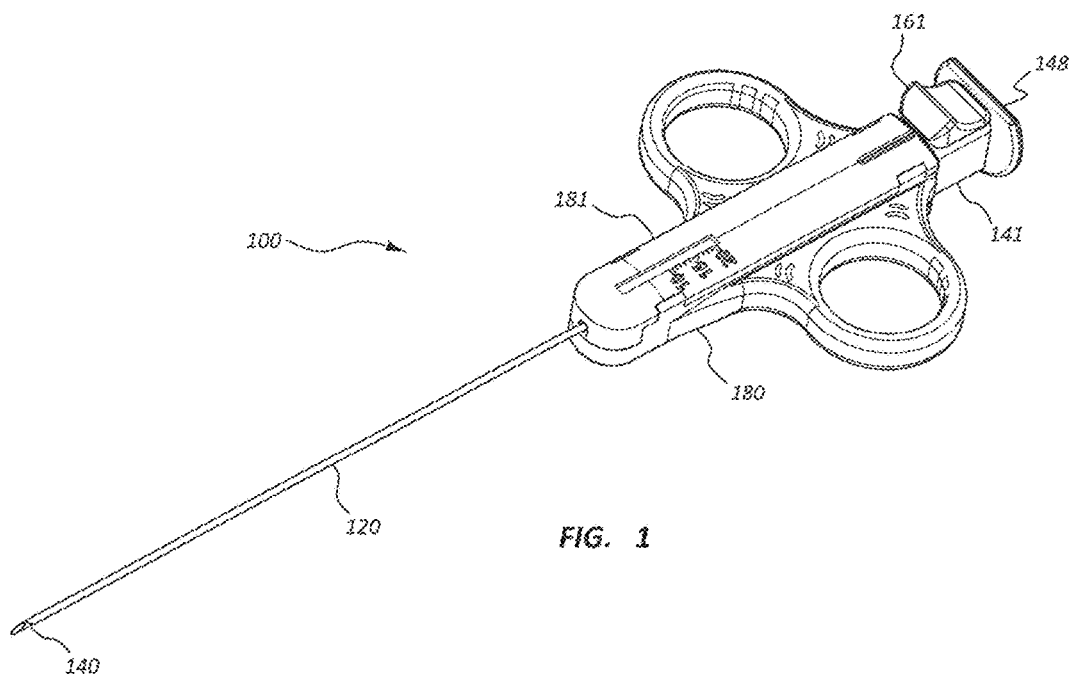
FIG. 1 is a perspective view of a biopsy needle device.

As described herein, systems and techniques are provided for color-coding medical instruments to yield safer and more accurate results. To better appreciate the overall systems and methods, the disclosure will be primarily described in connection with a biopsy needle. It will be understood, however, that many variations and uses of these systems and techniques are possible. As such, the biopsy needle embodiments described herein is merely exemplary and non-limiting.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. For example, as specifically applied to the needle portion of the biopsy needle device, the proximal end of the needle refers to the end nearest the handle or actuator and the distal end refers to the opposite end, the end that may be inserted into a patient. Likewise, "tissue" is used in its broadest sense, to refer to any tissue or substance within a human or animal body, and the procedures and techniques described herein may performed in vivo or in vitro.

Tissue biopsy devices may be configured to retrieve tissue samples from various locations within a patient's body. For example, a biopsy device may comprise a biopsy needle device, or needle assembly, including tubular members, needles, trocars, cutting styli, styli, cannula, and/or other components configured to access and sever a tissue sample in a medical procedure commonly referred to as Core Needle Biopsy. The biopsy needle device may be advanced to a location within the body through the skin of the patient (percutaneous access), through an open incision or through a body lumen or other structure. A portion of the biopsy needle device may be advanced into a lesion or target tissue. Another portion of the biopsy needle device may then be advanced into the lesion or target tissue to sever a tissue sample from the lesion or target tissue. The biopsy needle device may then be withdrawn from the patient and the tissue sample extracted from the needle assembly for analysis. Furthermore, a biopsy needle device may comprise a handle or actuator configured to axially displace or deflect at least a portion of the biopsy needle device such that the biopsy needle device cuts or severs the targeted tissue sample.

Figure 2:
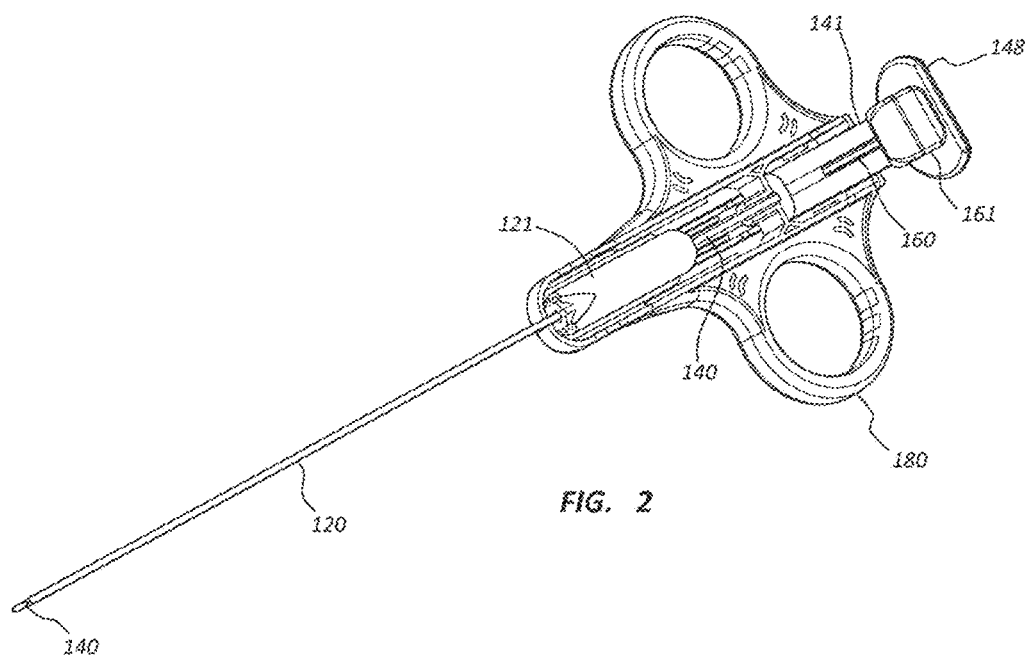
FIG. 2 is a cross-sectional view of the biopsy needle device of FIG. 1 with the housing lid removed.

FIGS. 1 and 2 are perspective views of a biopsy needle device 100. As illustrated, the biopsy needle device 100 may comprise a cannula assembly, a trocar assembly, a stylet assembly and an actuator. The cannula assembly may comprise a cannula 120 and a cannula hub 121. The trocar assembly may comprise a trocar 140 and a trocar hub 141. The stylet assembly may comprise a stylet 160 and a stylet hub 161. The actuator may comprise a housing base 180 and housing lid 181.

FIG. 3 is a perspective view of the cannula assembly of FIGS. 1 and 2, and FIG. 3A is a detail view of a distal end portion 122 of the cannula 120 of FIG. 3. Referring now to FIGS. 3 and 3A, in some embodiments the cannula assembly 102 may comprise the cannula 120 and the cannula hub 121. The cannula 120 may comprise an elongate tube having the distal end portion 122 and a proximal end portion 123. The cannula 120 may range in diameter from 8 gauge to 22 gauge and including from 14 gauge to 20 gauge. A lumen 124 of the cannula 120 may be sized to accommodate the positioning of the trocar 140 within the lumen 124. The length of the cannula 120 may range from 100 cm to 5 cm and including from 25 cm to 10 cm. The cannula 120 may be preferably manufactured from a medical grade stainless steel material.

In some embodiments the proximal end portion 123 of the cannula 120 may be configured to be fixedly coupled to the cannula hub 121 such that the proximal end of the lumen 124 is open to allow for passage of the trocar 140 into the lumen 124. The cannula 120 may be fixedly coupled to the cannula hub 121 using techniques known in the art such as bonding, welding, overmolding, etc. The outside surface of the proximal end portion 123 of the cannula 120 may be modified to enhance the coupling of the cannula 120 to the cannula hub 121. For example, the surface may be chemically or mechanically etched or textured to roughen the surface in order to enhance the adhesion of an adhesive or plastic. Alternatively, the surface may be chemically modified to enhance the adhesion of the adhesive or plastic.

The distal end portion 122 of the cannula 120 may comprise a bevel 125. The bevel 125 may be configured to cut or sever tissue as the cannula 120 slides along the longitudinal axis of the trocar 140. The bevel 125 may have an angle of from 180 degrees to 5 degrees and including from 30 degrees to 25 degrees. Bevel edges 126 may be sharp and may be configured to cut or sever tissue.

In certain embodiments the cannula 120 may comprise a plurality of indicia 135 configured to indicate to the practitioner a distance that the cannula 120 and trocar 140 have advanced into a body tissue (for clarity not all indicia 135 are labeled). For example, each indicium 135 may be positioned 1 cm apart; thus, if the practitioner displaces the cannula 120 and the trocar 140 into a body tissue up to the third indicia 135 from the distal end portion 142 of the trocar 140, it may indicate to the practitioner that approximately 3 cm of the trocar 140 and cannula 120 has been displaced into the body tissue. In some embodiments, the indicia 135 may comprise a plurality of substantially evenly spaced annular lines, marks, or grooves on an outside surface of the cannula 120. In certain embodiments, the indicia may comprise a plurality of tick marks or the indicia may not be evenly spaced.

The cannula hub 121 may comprise a body 127, a cannula coupling portion 128, a cavity 129 and locking teeth 130. The cannula hub 121 may be disposed within the distal end portion of the housing base 180 and be configured to move along a longitudinal axis of the housing base 180. A cannula coupling portion 128 may be generally cylindrical with a bore 136 having a diameter to accommodate the cannula 120 and a length to provide a secure attachment of the cannula 120 to the cannula coupling portion 128. The cannula coupling portion 128 may be positioned near a distal end 133 of the body 127 of the cannula hub 121. The cavity 129 may extend from the distal end 133 of the body 127 to a proximal end 132 of the body 127. The cavity 129 may be sized to accommodate a spring 182 configured to move the cannula assembly 102 from a proximal configuration to a distal configuration. The locking features, such as teeth 130 of the cannula hub 121, are configured to engage with opposing locking teeth 183 of the housing base 180. The engaging locking teeth 130, 183 may allow for the actuator 108 to be cocked and the cannula assembly 102 to be locked in a selected proximal position. The cannula hub 121 may further comprise a shoulder 134 near the proximal end 132 of the body 127. The shoulder 134 may be configured to engage with a hook member 153 of the trocar hub 141 to allow for cocking of the actuator 108 and selective positioning of the cannula assembly 102 in a proximal position. The cannula hub 121 may be formed from an opaque or translucent plastic material using manufacturing techniques known to the industry such as injection molding, casting, machining, etc.

FIG. 4 is a perspective view of the trocar assembly 104 of FIGS. 1 and 2, and FIG. 4A is a detail view of a distal end portion 142 of the trocar 140 of FIG. 4 taken from detail line 4A. Referring to FIGS. 4-4A, in some embodiments the trocar assembly 104 may comprise the trocar 140 and the trocar hub 141. The trocar 140 may comprise an elongate tube having the distal end portion 142 and a proximal end portion 143. The trocar 140 may range in diameters and lengths to match the cannula for optimized tissue cutting. The trocar 140 diameter may be configured such that the trocar 140 may be slidingly disposed within the lumen 124 of the cannula 120. The lumen 144 of the trocar 140 may be configured to accommodate the positioning of the stylet 160 within the lumen 144. The trocar 140 may be preferably manufactured from a medical grade stainless steel material.

The distal end portion 142 of the trocar 140 may comprise a bevel 156 and a notch 157. The bevel 156 may be configured to penetrate tissue as the trocar 140 may be inserted into the patient's tissue. The bevel 156 may be configured as any type of tissue penetrating bevel utilized in medical devices comprising a trocar. For example, the bevel 156 type may be a Tri-cut, Whitacre, pencil point, Seldinger, Sprotte, etc.

In some embodiments the notch 157 may be located proximal of the bevel 156. The notch 157 may have a length that is longer than a width. The length of the notch 157 may range from 5 cm to 35 cm and including embodiments where it is about 20 cm. The width of the notch 157 may be approximately equivalent to the outer diameter of the trocar 140. The depth of the notch 157 may be approximately one half of the outer diameter of the trocar 140. The notch 157 may be positioned proximal of the bevel 156. The notch 157 may comprise an open channel 158 having a semi-circular wall. The channel 158 may be configured to capture and retain the tissue sample cut or severed by the cannula (120 of FIG. 3). For example, the trocar 140 may be inserted into the target tissue or lesion. A portion of the target tissue or lesion may collapse into the channel 158. The cannula 120 may then be advanced over the trocar 140 cutting or severing the portion of the target tissue or the lesion from the surrounding tissue. The cut or severed tissue sample may be captured and retained within the channel 158.

In some embodiments the proximal end portion 143 of the trocar 140 may be configured to be fixedly coupled to the trocar hub 141 such that the proximal end of the lumen 144 is open to allow for passage of the stylet 160 into the lumen 144. The trocar 140 may be fixedly coupled to the trocar hub 141 using techniques known in the art such as bonding, welding, overmolding, etc. The outside surface of the proximal end portion 143 of the trocar 140 may be modified to enhance the coupling of the trocar 140 to the trocar hub 141. For example, the surface may be chemically or mechanically etched or textured to roughen the surface in order to enhance the adhesion of an adhesive or plastic. Alternatively, the surface may be chemically modified to enhance the adhesion of the adhesive or plastic.

In some embodiments the trocar hub 141 may comprise a body 145, a trocar coupling portion 146, a cavity 147, an actuation pad 148 and an actuation extension 149. The trocar hub 141 may be disposed within the proximal end portion of the housing base 180 and be configured to move along a longitudinal axis of the housing base 180. The trocar coupling portion 146 may be generally cylindrical with a diameter to accommodate the trocar 140 and a length to provide a secure coupling of the trocar 140 to the trocar coupling portion 146. The trocar coupling portion 146 may be positioned near a distal end 150 of the body 145 of the trocar hub 141. The cavity 147 may extend from the distal end 150 of the body 145 to a proximal end 151 of the body 145. The cavity 147 may be configured to accommodate a portion of the stylet hub 161. The body 145 may further comprise a longitudinal slot 152 configured to allow for distal and proximal movement of the stylet hub 161. The actuation extension 149 of the trocar hub 141 may extend distally from the body 145 of the trocar hub 141. The actuation extension 149 may comprise a hook member 153 at a distal end 154. The hook member 153 may be configured to engage the shoulder 134 of the cannula hub 121 such that proximal movement of the trocar assembly 104 may result in proximal movement of the cannula assembly 102. Additionally, the hook member 153 may be configured to engage with the cannula hub 121 such that the locking teeth 130 of cannula hub 121 may be disengaged from the locking teeth 183 of the housing base 180 allowing for the cannula assembly 102 to move distally. The actuation pad 148 may be located at the proximal end 151 of the body 145. The actuation pad 148 may be configured for placement of the practitioner's thumb or finger when activating the actuator 108. The actuation pad 148 may be configured to accommodate the practitioner's thumb or finger and may comprise a distally facing surface 155 configured to provide a non-slip surface. The surface 155 may comprise, but not limited to, ridges, grooves, detents and/or a textured surface. The trocar hub 141 may be formed from an opaque or translucent plastic material using manufacturing techniques known to the industry such as injection molding, casting, machining, etc.

In certain embodiments, a portion or portions of at least one of the components of the biopsy needle device 100, including, but not limited to, the cannula 120, the trocar 140, and/or the stylet 160, may comprise a radiopaque material and/or an echogenic material. A radiopaque material (for example, in combination with computed tomography or x-ray) may aid the practitioner in directing or displacing the biopsy needle device 100 to a desired or predetermined position within the body tissue of the patient. Bismuth, gold, or other radiopaque materials alone, or in combination, may be used. An echogenic material or surface (for example, in combination with ultrasound) may analogously aid the practitioner in directing or displacing the trocar assembly 104 to a desired or predetermined position within the body tissue of the patient. Surface disruptions such as texturing, grooves, dimples, or a combination of materials may also be used.

Figure 5A:
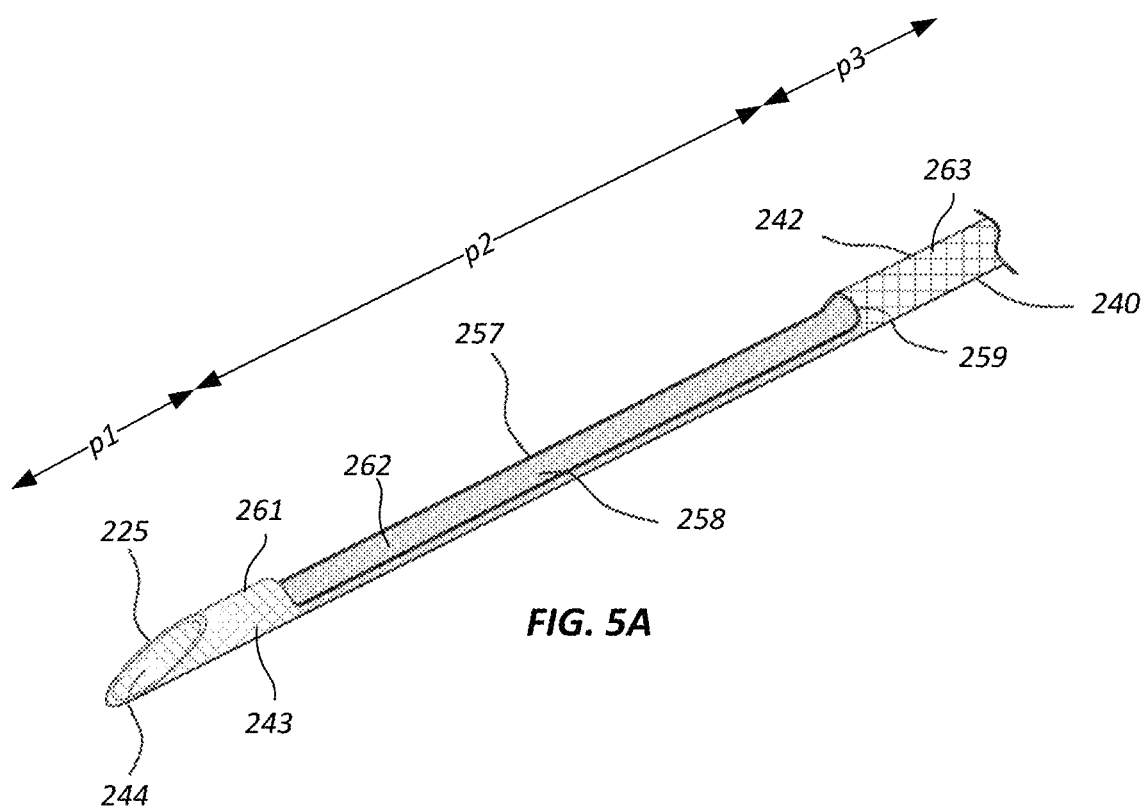
FIGS. 5A-B are perspective views of a color-coded biopsy needle.

In at least some examples, portions of a device may be coated, embedded with, or other formed of echogenic materials having different properties. For example, as shown in FIG. 5A, trocar 240 may comprise an elongate tube having the distal end portion 242 and a proximal end portion 243. The trocar 240 may range in diameters and lengths to match the cannula for optimized tissue cutting. The trocar 240 diameter may be configured such that the trocar 240 may be slidingly disposed within a lumen of a cannula. The lumen 244 of the trocar 240 may be configured to accommodate the positioning of a stylet within the lumen 244. The trocar 240 may be preferably manufactured from a medical grade stainless steel material. As shown here, the distal end portion 242 of the trocar 240 may comprise a bevel 225 and a notch 257 in channel 258. The bevel may be configured to penetrate tissue as the trocar 240 may be inserted into the patient's tissue. The bevel may be configured as any type of tissue penetrating bevel utilized in medical devices comprising a trocar. For example, the bevel type may be a Tri-cut, Whitacre, pencil point, Seldinger, Sprotte, etc.

In this example, the trocar is divided into three distinct portions p1, p2, p3 and each of the three portions may be coated or formed of a material with unique echogenic properties. As shown here, portion p1 is coated with first material 261, portion p2 is coated with second material 262 and portion p3 is coated with third material 263, the three materials 261-263 having different echogencities. The materials 261-263 are shown with three patterns by way of illustrations, although it will be understood that the materials may be imperceptible to the naked eye and that the color-coding materials may only be differentiated under ultrasound. In at least some examples, the materials may include microbubbles in a biocompatible plastic coating and the difference in echogenicity may be a difference in percentage (e.g., 10%, 20%, 30% or 40% difference in echogenicity between materials). In at least some examples, the materials may include one or more textured metals, and difference between the textures (e.g., the higher the density of notches, reflectors or other surface featured on the textured metal) may result in differences in echogenicity and/or may result in different colors as will be described in greater detail below. In at least some examples, echogenic coatings having microbubbles are used to color-code one or more devices, and the portions of the device may be differentiated based on the microbubble density of each segment. In at least some examples, the higher the density of the microbubbles, the greater the echogenicity of the portion of the device coated with the microbubbles.

Figure 6:
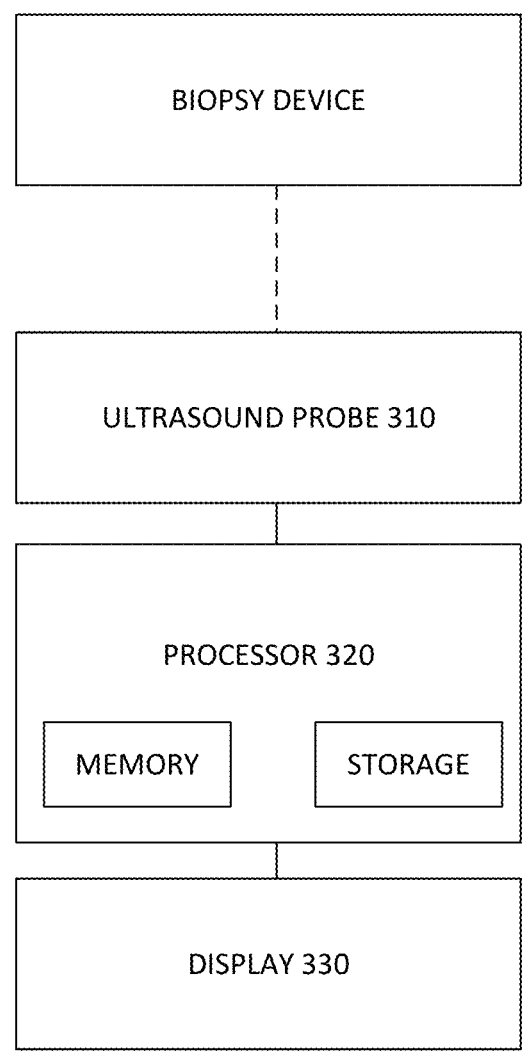
FIG. 6 is a schematic showing a system for color-coding.
Figure 7A:
FIGS. 7A-B are photographs showing breast mass biopsy without and with color-coding.
Figure 7B:
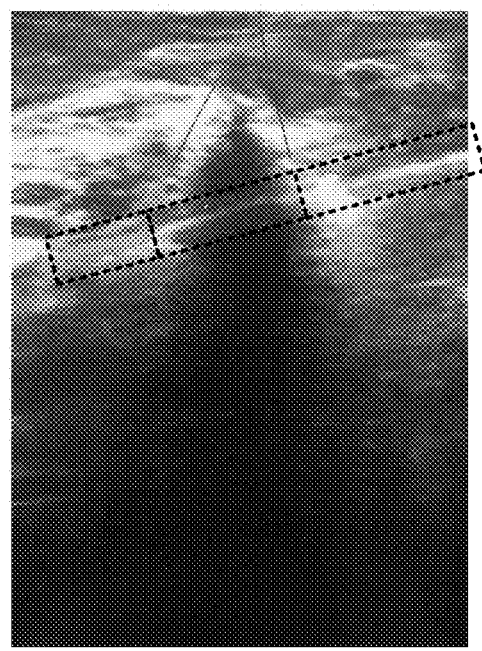
Figure 8A:
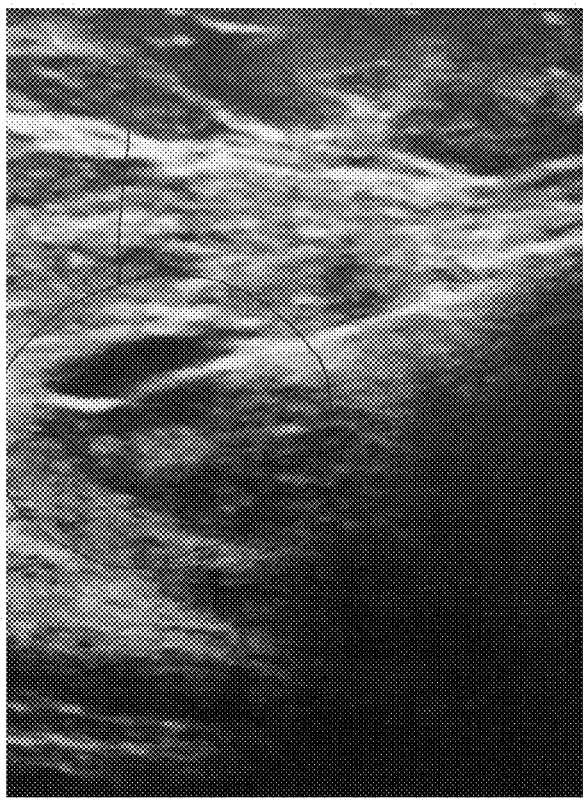
FIGS. 8A-B are photographs showing ultrasound-guided lymph node biopsy without and with color-coding.
Figure 8B:
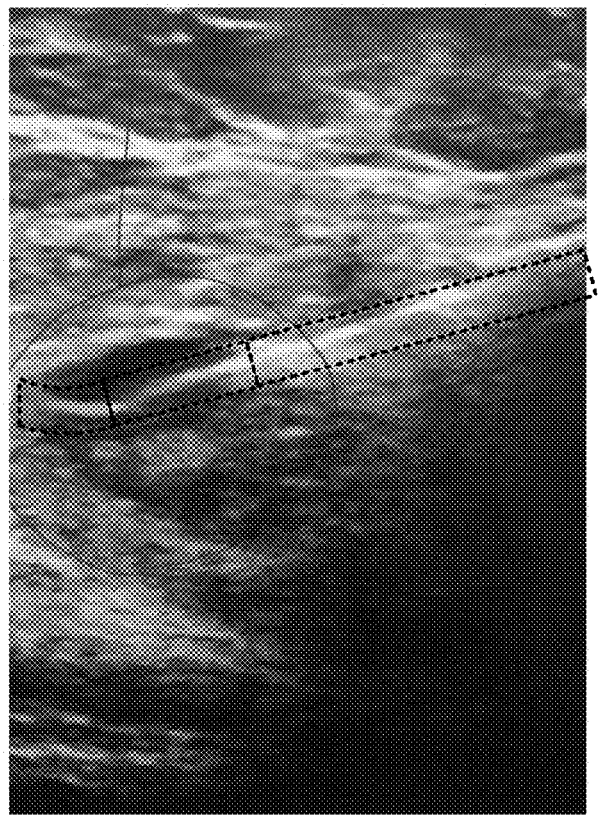

As shown in FIG. 6, an ultrasound device 310 may be used to image biopsy needle 100 within tissue, the ultrasound device 310 being in communication, either wirelessly or via a wired connection, to a processor 320 having a memory and storage, which in turn is coupled to a display 330. Processor 330 may be configured and arranged to collect images from the ultrasound probe 310 and color code certain segments of the biopsy device based on the different echogenic coatings, surface texture and/or surface contour. For example, portion p1 having a first echogenicity may be imaged and color-coded to a first color (e.g., red) based on the first echogenicity, portion p2 having a second echogenicity may be imaged and color-coded to a second color (e.g., blue) based on the second echogenicity and portion p3 having a third echogenicity may be imaged and color-coded to third color (e.g., orange) based on the third echogenicity. This color-coding may be sent to the display and overlaid on the raw ultrasound image such that the device (e.g., biopsy needle), which was previously grayscale, now appears as having three distinct segments, each of the segments appearing in a different color. In at least some examples, the display will process the raw image to add the colors or combine the raw image with the color mapped data to yield an at least partially colored image. It will be understood that a device may be coated with only one material or more multiple materials, and divided into only one portion or multiple portions of different echogenicities. Additionally, distinct devices may be coated with different materials so that the processor can recognize them as being distinct, correlating each echogenicity with a color, color-coding the distinct devices and showing them in different colors on a display so that the location of different medical devices may be quickly recognized.

Turning back to FIG. 5A, color-coding may be performed using other techniques. For example, as shown in FIG. 5A, three materials 261-263 may be used to produce the color-coding materials. Instead of having different echogenic materials or textured surfaces, the surface contours of a device may be used to provide the color-coding. For example, a processor 320 may be configured to recognize certain features of a device based on an intended procedure. The ability of the processor to recognize the features may include artificial intelligence or machine learning techniques. For example, a processor may be fed a training set, which may be a large dataset that includes photographs of different types of biopsy needles from different angles. The initial dataset may also include labels of the different portions of the device (e.g., lumen, trocar, bevel, notch, channel, etc.). The processor may utilize feature extraction to create an algorithm to predict certain features in a device, such as a biopsy needle. Using these techniques, the system may learn to identify portions of a device (e.g., a notch of a biopsy needle), and consistently color-code those features on the display.

Figure 5B:
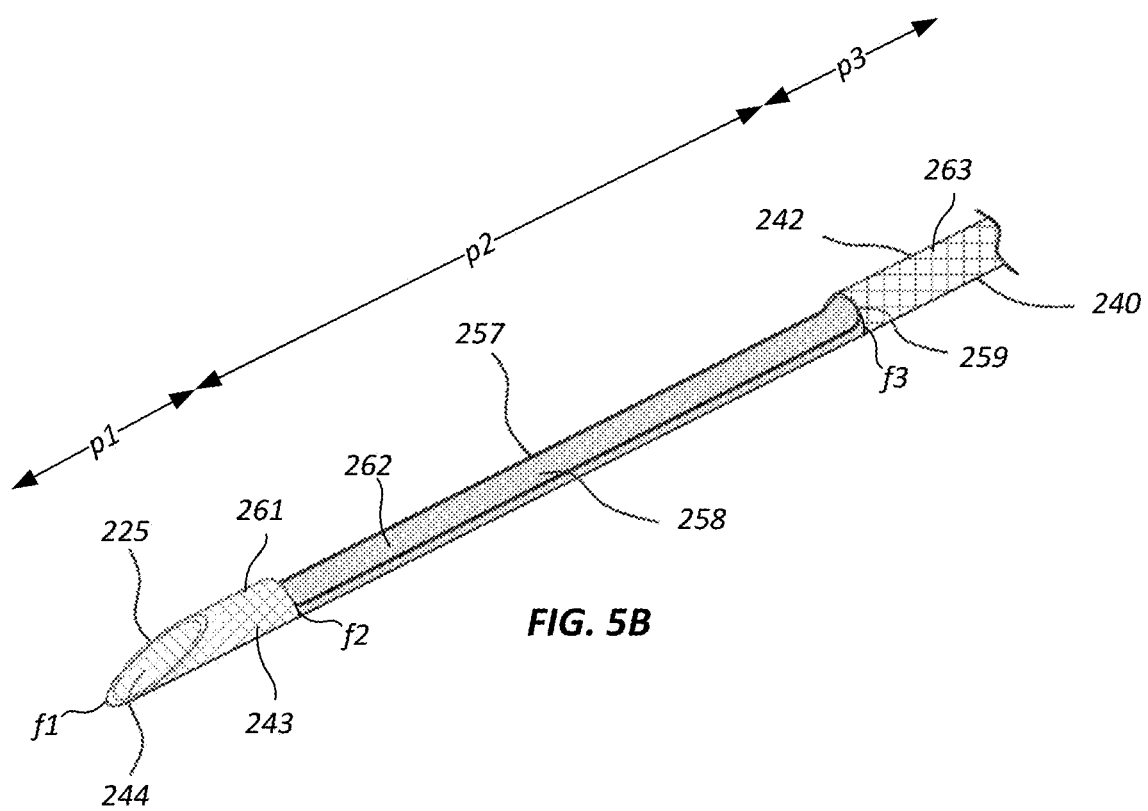

In yet another example, certain physical parameters of a device may determine the color-coding. For example, a processor may be instructed to identify certain features (e.g., the distal end and/or the proximal ends) of a biopsy needle based on echogenic foci. In some examples, the echogenic foci will consist of focal echogenic coating and/or focal textured areas along predetermined locations on the needle. Using techniques such as artificial intelligence and deep learning, the software of the processor may identity and/or detect abnormally high echoes and use them as a map for color coding. The echogenic foci along the needle may be the same or may provide increasing echoes (i.e., increased echogenicity) from one to the device toward the other (e.g., increased echogenicity from a location toward the distal tip of the needle) towards the tip of the needle. If the system knows that the total length of the needle is 10 cm or 16 cm, then it may color code the entire length, or a preterminal portion of the length. For example, the system may be configured to color code the first ¼ of the length or the first 5 cm of a biopsy device with a first color, the second segment with a second color, and so on. In FIG. 5B, three foci, f1, f2 and f3 are shown at the distal tip of the needle and on either end of notch 257, respectively. In this example, the foci are circumferentially extending bands, and the system may be configured to locate these foci and color the segment of the device between the foci with a specific color (e.g., green). Thus, the system may be configured to color the segment from f1 to f2 in a first color (e.g., red), from f2 to f3 in a second color (e.g., green) and from f3 to the proximal end of the device in a third color (e.g., blue).

Figure 9A:
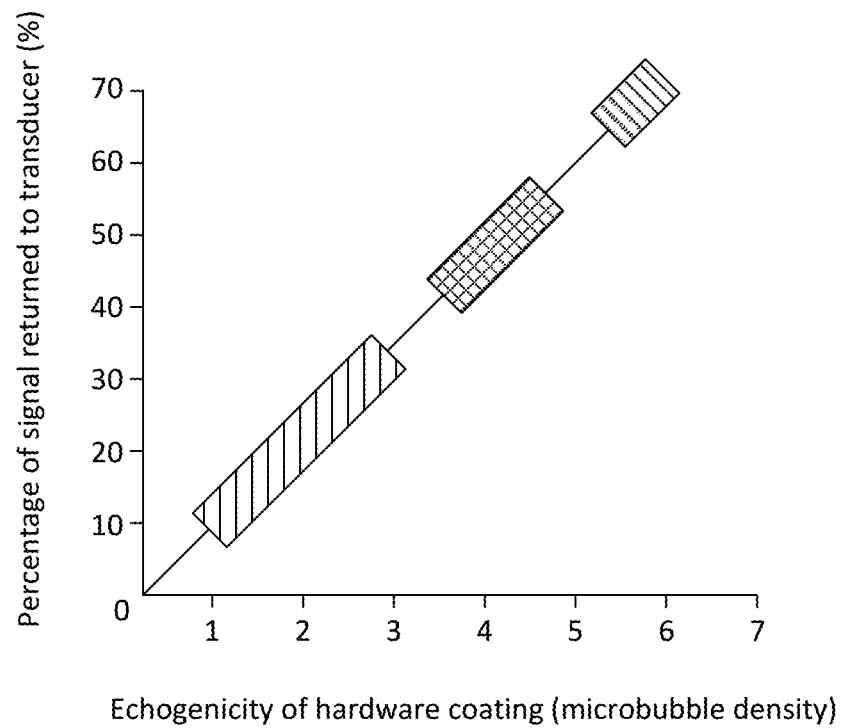
FIGS. 9A-B are a graph showing echogenicity of hardware coating vs. percentage of signal returned and another example of a biopsy device.
Figure 9B:
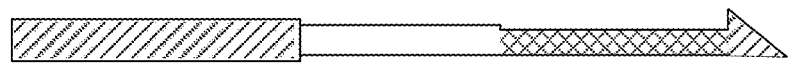

FIGS. 7A-B and 8A-B are photographs showing breast mass biopsy without and with color-coding, and ultrasound-guided lymph node biopsy without and with color-coding. For the sake of clarity, the color-coded sections are outlined with dashed rectangular perimeters on the display screen, which may or may not be visible to the user. As shown, color-coding devices via segments of distinct echogenicity aids the operator in identifying portions of the device in relation to certain landmarks. FIGS. 9A-B are a graph showing echogenicity of hardware coating vs. percentage of signal returned and another example of a biopsy device with certain segments correlated to the echogenicity of FIG. 9A.

Figure 10:
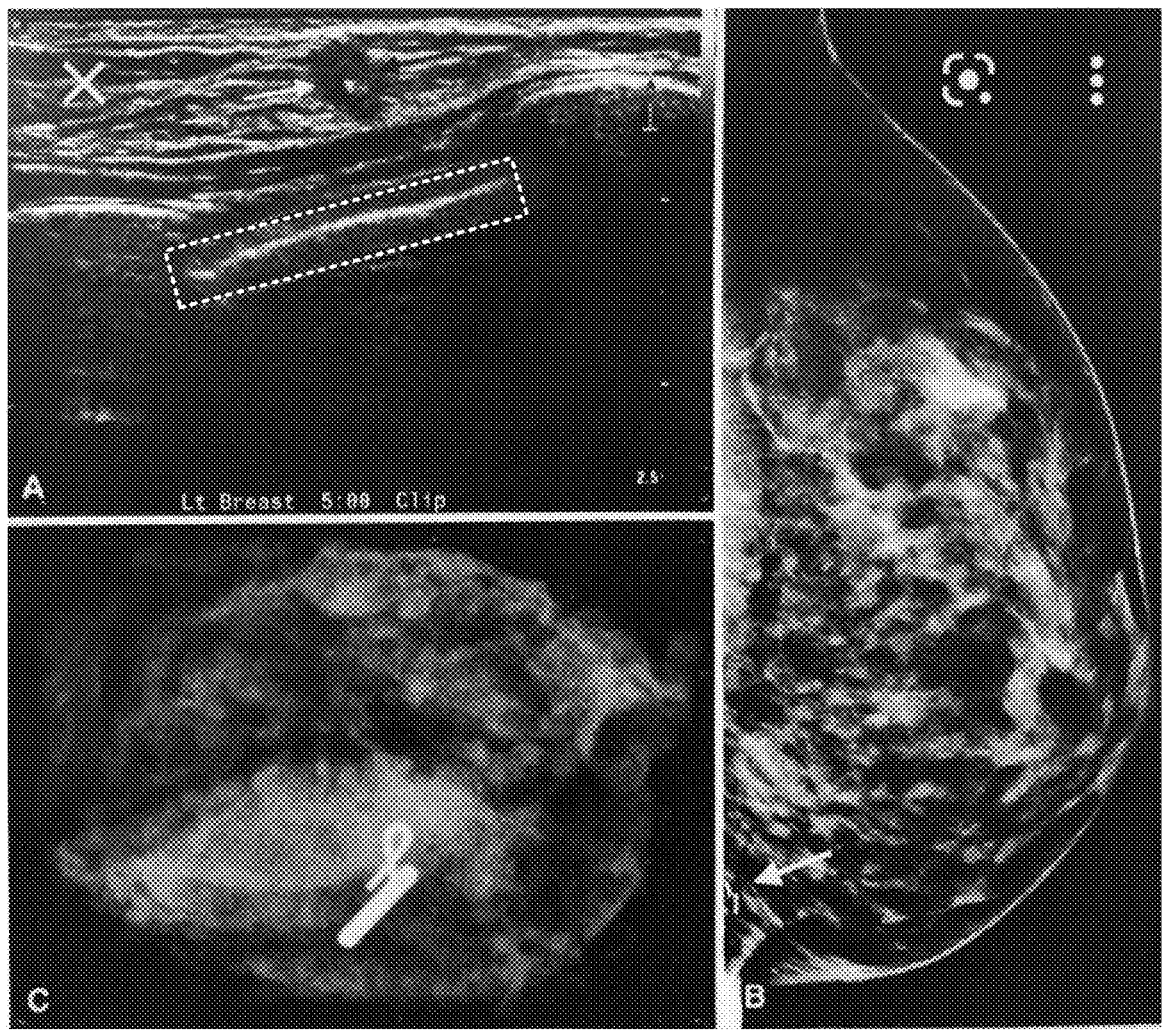
FIG. 10 is an example of color-coding an RFID tag.
Figure 11A:
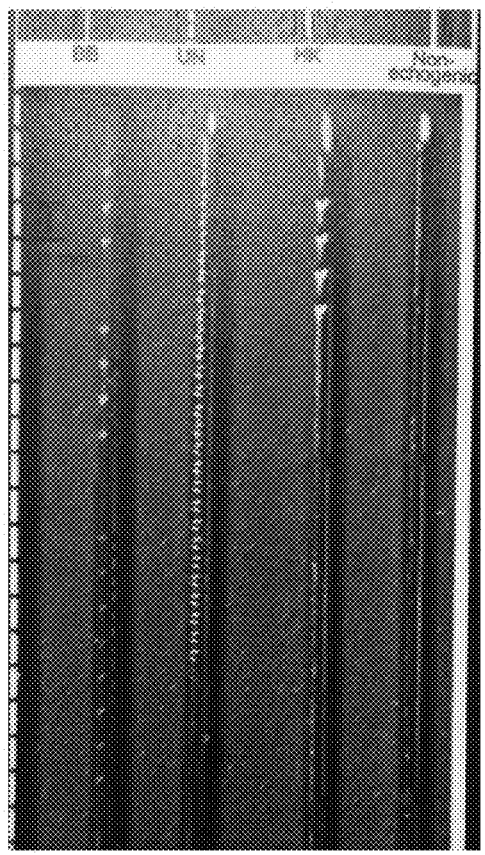
FIGS. 11A-B are examples of color-coding a textured needle and ultrasounds showing same.
Figure 11B:
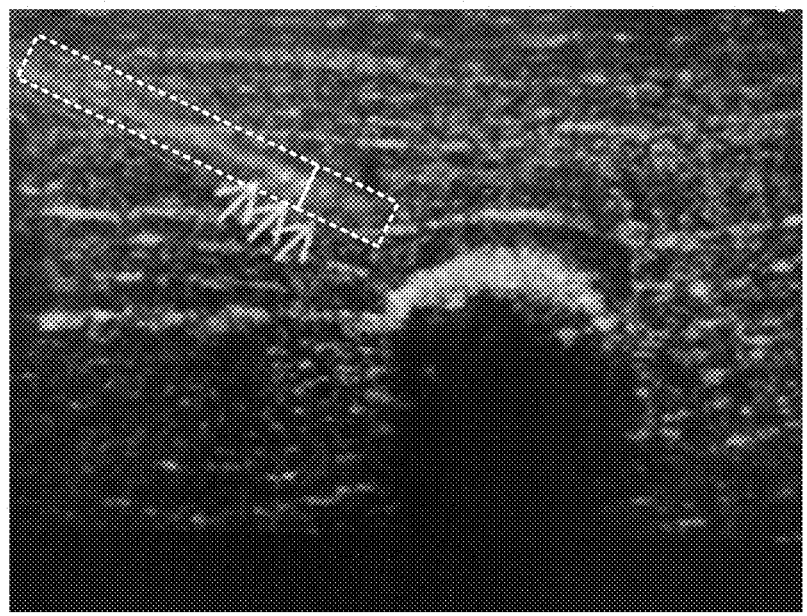

Though a biopsy needle has been discussed, it will be appreciated that other devices can be likewise color-coded. For example, biopsy RFID tags and/or Biopsy markers may also be color-coded via coatings or varying materials and the processor may automatically display the tags in a specific color (e.g., red, or blue) for faster and easier identification (FIG. 10). Additionally, color-coding may also be used for textured needles (FIGS. 11A-B). Thus, it will be understood that the techniques and systems described herein may be used in connection with any medical device or instrument that is placed at least partially within the body, such as biopsy needles, including vacuum-assisted breast biopsy devices, breast biopsy needles, placement, location and retrieval of biopsy clips and/or markers, placement, location and retrieval of RFID clips and/or markers, biopsies of the head, face, chest, abdomen (liver, kidneys), pelvis and/or extremities, lymph node biopsies, vascular access devices (central lines, PICC lines, peripheral lines), stents, filters, angioplasty, drains and drainage catheters.

Color-coding instruments may improve ultrasound-guided procedure safety and accuracy. Using these techniques, the physician may, for example, better appreciate the location of a biopsy device tip, reducing the risk of injury to the patient (e.g., risk of causing a pneumothorax or vascular injury). The physician may also better appreciate the location of a biopsy trough leading to more accurate biopsies of suspicious lesions and less false negative biopsies. In at least some examples, a method of color-coding a medical procedure may include providing a medical device comprising at least one segment having an echogenic coating, imaging the medical device via an ultrasound probe, collecting images via a processor from the ultrasound probe, color coding the at least one segment based on the echogenic coating, and displaying a color-coded image. In at least some examples, a method of color-coding a medical procedure may include imaging a medical device via an ultrasound probe, collecting images via a processor from the ultrasound probe, locating the medical device in a collected image and identifying at least one segment having an echogenic coating, color coding the at least one segment based on the echogenic coating, and displaying a color-coded image.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

We claim:

1. A computer-implemented method for using machine-learning-based image analysis to colorize a biopsy device in medical imaging, the method comprising:
   obtaining ultrasound medical imaging of anatomy of a patient, the ultrasound medical imaging including a depiction of a medical device within the anatomy of the patient;
   generating a segmentation of the medical device by inputting the ultrasound medical imaging into a trained machine-learning model that has been trained, based on (i) a plurality of training ultrasound images of medical devices and (ii) labels of different portions of the medical devices, to learn associations between the labels and the different portions of the medical devices, such that the trained machine-learning model is configured to use the learned associations to segment the depiction of the medical device in the ultrasound medical imaging into one or more portions corresponding to the labels;
   modifying the ultrasound medical imaging by applying a color-coding to the depiction of the medical device based on the generated segmentation; and
   causing a display to output the modified ultrasound medical imaging.

2. The computer-implemented method of claim 1, wherein:
   the segmentation of the medical device includes a plurality of portions; and
   the color-coding includes a different color for each of the plurality of portions.

3. The computer-implemented method of claim 1, wherein the labels include surface contours of the different portions, such that the trained machine-learning model is configured to determine surface contours for the one or more portions of the medical device based on the corresponding labels.

4. The computer-implemented method of claim 3, wherein:
   the medical device is a biopsy device; and
   each of the different portions is selected from a group consisting of a lumen of the biopsy device, a trocar of the biopsy device, a bevel of the biopsy device, a notch of the biopsy device, and a channel of the biopsy device.

5. The computer-implemented method of claim 1, wherein:
   the medical device is a biopsy device;
   the labels include one or more foci of the biopsy device; and,
   each of the one or more foci is selected from a group consisting of a distal tip of a needle of the biopsy device, a distal end of a notch of the biopsy device, and a proximal end of the notch.

6. The computer-implemented method of claim 1, wherein:
   each of the different portions of the medical device has a respective echogenicity that is different than each other; and
   the labels are based on the respective echogenicities, such that the trained machine-learning model is further configured to segment the depiction of the medical device in the ultrasound medical imaging into one or more portions based on relative echogenicity of the one or more portions.

7. The computer-implemented method of claim 1, wherein:
   generating the segmentation of the medical device further includes inputting one or more dimensions of the medical device into the trained machine-learning model; and
   the trained machine-learning model is further configured to segment the depiction of the medical device in the ultrasound medical imaging into the one or more portions based on the input one or more dimensions.

8. The computer-implemented method of claim 7, wherein at least one of the one or more portions includes a region of the medical device not visible in the ultrasound medical imaging, the not visible region included in the at least one portion by the trained machine-learning model based on the input one or more dimensions of the medical device.

9. The computer-implemented method of claim 1, wherein:
   the medical device is a biopsy device; and
   the color-coding includes a visual indication of a notch of the biopsy device at which a biopsy sample is to be collected.

10. A system for using machine-learning-based image analysis to colorize a biopsy device in medical imaging, comprising:
- at least one memory storing instructions;
- a display; and
- at least one processor operatively connected to the at least one memory and to the display, and configured to execute the instructions to perform operations, including:
  - obtaining medical imaging of anatomy of a patient, the medical imaging including a depiction of a medical device within the anatomy of the patient;
  - generating a segmentation of the medical device by inputting the medical imaging into a trained machine-learning model that has been trained, based on (i) a plurality of training images of medical devices and (ii) labels of different portions of the medical devices, to learn associations between the labels and the different portions of the medical devices, such that the trained machine-learning model is configured to use the learned associations to segment the depiction of the medical device in the medical imaging into one or more portions corresponding to the labels;
  - modifying the medical imaging by applying a color-coding to the depiction of the medical device based on the generated segmentation; and
  - causing the display to output the modified medical imaging.

11. The system of claim 10, wherein:
the segmentation of the medical device includes a plurality of portions; and
the color-coding includes a different color for each of the plurality of portions.

12. The system of claim 10, wherein:
the medical device is a biopsy device;
the labels correspond to one or more of surface contours of the different portions, foci associated with the different portions, or different echogenicities of the different portions; and
each of the different portions is selected from a group consisting of a lumen of the biopsy device, a trocar of the biopsy device, a bevel of the biopsy device, a notch of the biopsy device, and a channel of the biopsy device.

13. The system of claim 12, wherein:
the medical device is a biopsy device;
the labels include one or more foci of the biopsy device; and
each of the one or more foci is selected from a group consisting of a distal tip of a needle of the biopsy device, a distal end of a notch of the biopsy device, and a proximal end of the notch.

14. The system of claim 10, wherein:
generating the segmentation of the medical device further includes inputting one or more dimensions of the medical device into the trained machine-learning model;
the trained machine-learning model is further configured to segment the depiction of the medical device in the medical imaging into the one or more portions based on the input one or more dimensions; and
at least one of the one or more portions includes a region of the medical device not visible in the medical imaging, the not visible region included in the at least one portion by the trained machine-learning model based on the input one or more dimensions of the medical device.

15. The system of claim 10, wherein:
the medical device is a biopsy device; and
the color-coding includes a visual indication of a notch of the biopsy device at which a biopsy sample is to be collected.

16. A non-transitory computer-readable medium comprising instruction for using machine-learning-based image analysis to colorize a biopsy device in ultrasound medical imaging, the instructions being executable by at least one processor to perform operations, including:
- obtaining ultrasound medical imaging of anatomy of a patient, the medical imaging including a depiction of a biopsy device within the anatomy of the patient;
- generating a segmentation of the biopsy device by inputting the ultrasound medical imaging into a trained machine-learning model that has been trained, based on (i) a plurality of training ultrasound images of biopsy devices and (ii) labels of different portions of the biopsy devices, to learn associations between the labels and the different portions of the biopsy devices, such that the trained machine-learning model is configured to use the learned associations to segment the depiction of the biopsy device in the ultrasound medical imaging into one or more portions corresponding to the labels;
- modifying the ultrasound medical imaging by applying a color-coding to the depiction of the biopsy device based on the generated segmentation; and
- causing a display to output the modified ultrasound medical imaging.

17. The non-transitory computer-readable medium of claim 16, wherein:
the segmentation of the biopsy device includes a plurality of portions;
the color-coding includes a different color for each of the plurality of portions; and
the color-coding further includes a visual indication of a notch of the biopsy device at which a biopsy sample is to be collected.

18. The non-transitory computer-readable medium of claim 16, wherein:
the labels include surface contours of the different portions, such that the trained machine-learning model is configured to determine surface contours for the one or more portions of the biopsy device based on the corresponding labels; and
each of the different portions is selected from a group consisting of a lumen of the biopsy device, a trocar of the biopsy device, a bevel of the biopsy device, a notch of the biopsy device, and a channel of the biopsy device.

19. The non-transitory computer-readable medium of claim 16, wherein:
the labels include one or more foci of the biopsy device; and
each of the one or more foci is selected from a group consisting of a distal tip of a needle of the biopsy device, a distal end of a notch of the biopsy device, and a proximal end of the notch.

20. The non-transitory computer-readable medium of claim 16, wherein:
generating the segmentation of the biopsy device further includes inputting one or more dimensions of the biopsy device into the trained machine-learning model;

the trained machine-learning model is further configured to segment the depiction of the biopsy device in the ultrasound medical imaging into the one or more portions based on the input one or more dimensions; and at least one of the one or more portions includes a region of the biopsy device not visible in the ultrasound medical imaging, the not visible region included in the at least one portion by the trained machine-learning model based on the input one or more dimensions of the biopsy device.

\* \* \* \* \*